US010905348B2

(12) United States Patent
Grunwald et al.

(10) Patent No.: US 10,905,348 B2
(45) Date of Patent: Feb. 2, 2021

(54) USER INTERFACES FOR MOBILE AND WEARABLE MEDICAL DEVICES

(71) Applicant: Bard Access Systems, Inc., Salt Lake City, UT (US)

(72) Inventors: Sorin Grunwald, Bucharest (RO); Isabella Barbara Hurezan, Bucharest (RO)

(73) Assignee: Bard Access Systems, Inc., Salt Lake City, UT (US)

( * ) Notice: Subject to any disclaimer, the term of this patent is extended or adjusted under 35 U.S.C. 154(b) by 80 days.

(21) Appl. No.: 14/800,716

(22) Filed: Jul. 16, 2015

(65) Prior Publication Data
US 2015/0317810 A1    Nov. 5, 2015

Related U.S. Application Data

(60) Provisional application No. 62/027,801, filed on Jul. 23, 2014.

(51) Int. Cl.
*A61B 5/0456* (2006.01)
*G06T 11/20* (2006.01)
(Continued)

(52) U.S. Cl.
CPC .......... *A61B 5/0456* (2013.01); *A61B 5/0452* (2013.01); *A61B 34/25* (2016.02);
(Continued)

(58) Field of Classification Search
CPC .... A61N 1/37282; A61B 5/7282; A61B 8/00; A61B 5/0422
See application file for complete search history.

(56) References Cited

U.S. PATENT DOCUMENTS 6,325,756 B1 * 12/2001 Webb ................. A61N 1/37282
128/904
2002/0173721 A1 * 11/2002 Grunwald ................ A61B 8/00
600/437
(Continued)

OTHER PUBLICATIONS

Cardionetics Cardiac Intelligence, 2013 ;.*
(Continued)

*Primary Examiner* — Ming Wu
(74) *Attorney, Agent, or Firm* — Rutan & Tucker LLP

(57) ABSTRACT

Graphical layouts, algorithms, and methods are introduced herein to implement user interfaces for mobile and/or wearable medical devices. In one aspect of the present invention, new graphical layouts are introduced for simplified presentation of time-dependent patient data. In another aspect of the invention, methods and algorithms are introduced to acquire, extract and present relevant features of patient data in real-time in order to simplify the graphical presentation and interpretation. In another aspect of the invention, elements of a multi-modal user interface are introduced in order to simplify and minimize the user's interaction with the medical wearable device. In yet another aspect of the invention, further methods are introduced for real-time interaction between a user or several users and a wearable or several wearable medical devices. In one embodiment of the present invention, a smartphone, a smart watch, a head-mounted device or similar devices can be used to acquire and display in real-time patient data, e.g., electrocardiogram and relevant features, e.g., heart rate, etc. In another embodiment of the present invention, smartphones, smart watches, head-mounted devices or similar devices can be used to share in real-time the patient data.

26 Claims, 8 Drawing Sheets

(51) Int. Cl.
*A61B 5/0452* (2006.01)
*G06F 3/01* (2006.01)
*A61B 34/00* (2016.01)
*G16H 40/63* (2018.01)
*A61B 5/00* (2006.01)
*A61B 90/50* (2016.01)

(52) U.S. Cl.
CPC .............. *G06F 3/011* (2013.01); *G06F 3/015* (2013.01); *G06T 11/206* (2013.01); *A61B 5/742* (2013.01); *A61B 2090/502* (2016.02); *A61B 2560/0487* (2013.01); *G06F 2203/0381* (2013.01); *G16H 40/63* (2018.01)

(56) References Cited

U.S. PATENT DOCUMENTS

| | | | | |
|---|---|---|---|---|
| 2003/0016851 | A1* | 1/2003 | Kaufman | A61B 6/5264 382/131 |
| 2009/0171227 | A1* | 7/2009 | Dziubinski | A61B 5/0452 600/516 |
| 2009/0240158 | A1* | 9/2009 | Hamilton | G06F 19/3406 600/511 |
| 2010/0228311 | A1* | 9/2010 | Naqvi | A61B 5/02233 607/18 |
| 2010/0312095 | A1* | 12/2010 | Jenkins | A61B 34/20 600/411 |
| 2010/0331712 | A1* | 12/2010 | Rothenberg | A61B 5/0422 600/509 |
| 2011/0092838 | A1* | 4/2011 | Helfenbein | A61B 5/0468 600/516 |
| 2013/0211214 | A1* | 8/2013 | Olsen | A61B 5/742 600/316 |
| 2013/0324870 | A1* | 12/2013 | Rajagopalan | A61B 5/044 600/523 |
| 2014/0221845 | A1* | 8/2014 | Mestha | A61B 5/7282 600/473 |
| 2015/0018632 | A1* | 1/2015 | Khair | A61B 5/029 600/301 |

OTHER PUBLICATIONS

Paul Obrien, Cell Phone Battery Level Indicator, Mar. 29, 2013;.*
Project Wish, Linux X10 universal device driver, Jul. 16, 2012.*
Electrocardiography—Wikipedia.*
Introduction to the ECG, , 2013.*

* cited by examiner

Fig. 5

510 — $$S_x = \sqrt{\frac{\sum_{i=1}^{n}(x_i - \bar{x})^2}{n-1}}$$

520 — $$C_x = \sqrt{\frac{\sum_{j=1}^{n}(x_{i,j} - \bar{x}_i)(x_{i-1,j} - \bar{x}_{i-1})}{S_{x_i} S_{x_{i-1}}}}$$

530 — $$\Sigma_M = A_M + P_{M+} + P_{M-} + T_M$$

540 — $$\bar{x} = \frac{\sum_{i=1}^{n} x_i}{n}$$

USER INTERFACES FOR MOBILE AND WEARABLE MEDICAL DEVICES

This application claims priority to U.S. Provisional Patent Application Ser. No. 62/027,801 filed on Jul. 23, 2014, the disclosure of which is incorporated herein by reference in its entirety.

FIELD OF THE INVENTION

The invention relates in general to simplified user interfaces for medical devices and in particular to simplified user interfaces which can be used for mobile and/or wearable medical devices. In the context of the present invention, mobile medical devices are medical devices which make use of mobile platforms, e.g., smartphones or tablets. In the context of the present invention, wearable medical devices are medical devices which make use of wearable platforms, e.g., smart watches, head-mounted devices, contact lenses, and other wearable objects integrating medical technology functions, etc. The invention introduces algorithms and methods which allow for the real-time data acquisition and extraction of relevant features of the clinical data for simplified presentation and interpretation. The invention further introduces graphical layouts optimized for the real-time display of clinical data on mobile platforms, e.g., smartphones, smart watches, head-mounted devices, and similar wearable devices. The invention further introduces methods of real-time interaction between users and wearable medical devices in order to allow for simplified interaction and easy sharing of clinical data.

BACKGROUND OF THE INVENTION

Currently there exists a growing tendency to use mobile platforms and wearable devices for medical applications. With such devices, the user interface paradigm is changing in several ways when compared to traditional medical devices. For example, the display/screen becomes smaller with mobile platforms and wearable devices, if a display exists at all. With mobile platforms and wearable devices, a range of different and/or new user interaction methods become more frequent compared with traditional medical devices, e.g., touch screens, voice control, gesture control. With mobile platforms and wearable devices, the ability to access information at remote locations and to share information in real-time increases when compared to traditional medical devices. For all the above mentioned reasons, new user interfaces for wearable and mobile medical devices are needed in order to optimize the real-time interaction, acquisition, presentation and interpretation of medical information using the new paradigm of mobile and wearable technology.

Several U.S. patents and patent applications describe aspects of using portable, mobile and wearable devices for medical applications. For example, in U.S. Pat. No. 7,261,691 "Personalized Emergency Medical Monitoring and Transmission System", a portable medical system for real-time applications is described without any emphasis on its user interface. In U.S. Pat. No. 8,326,651 a user interface is described for managing medical data focused on off-line use, i.e., not in real-time. In U.S. Pat. No. 8,521,122 a user interface for mobile devices is introduced for displaying emergency information. However, this invention does not address any aspects regarding the real-time acquisition of patient data nor does it address aspects related to extracting relevant information in order to simplify the user interface. U.S. 2011/0015496 describes the use of a mobile communication device for real-time patient data acquisition. No emphasis is placed on optimizing the user interface of the mobile device for its intended use. In U.S. 2011/0306859 a multipurpose, modular platform for mobile medical instrumentation is described including the use of a cell phone or tablet computer for real-time patient data acquisition. Once again, no emphasis is placed on optimizing the user interface of the mobile device for its intended use.

SUMMARY OF THE INVENTION

Graphical layouts, algorithms, and methods are introduced herein to implement new user interfaces for mobile and/or wearable medical devices. In one aspect of the present invention, graphical layouts are introduced for simplified presentation of time-dependent patient data. In another aspect of the invention, methods and algorithms are introduced to acquire, extract and present relevant features of patient data real-time in order to simplify the graphical presentation and interpretation. In another aspect of the invention, elements of a multi-modal user interface are introduced in order to simplify and minimize the user's interaction with the medical wearable device. In yet another aspect of the invention, further methods are introduced for real-time interaction between a user or several users and a wearable or several wearable medical devices. In one embodiment of the present invention, a smartphone, a smart watch, a head-mounted device or similar devices can be used to acquire and display in real-time patient data, e.g., electrocardiogram and relevant features, e.g., heart rate, etc. In another embodiment of the present invention, smartphones, smart watches, head-mounted devices or similar devices can be used to share in real-time the patient data.

BRIEF DESCRIPTION OF THE DRAWINGS

FIG. 5: Some algorithms used to support relevant feature extraction from patient data according to the present invention.

DETAILED DESCRIPTION OF THE INVENTION

Figure 1:
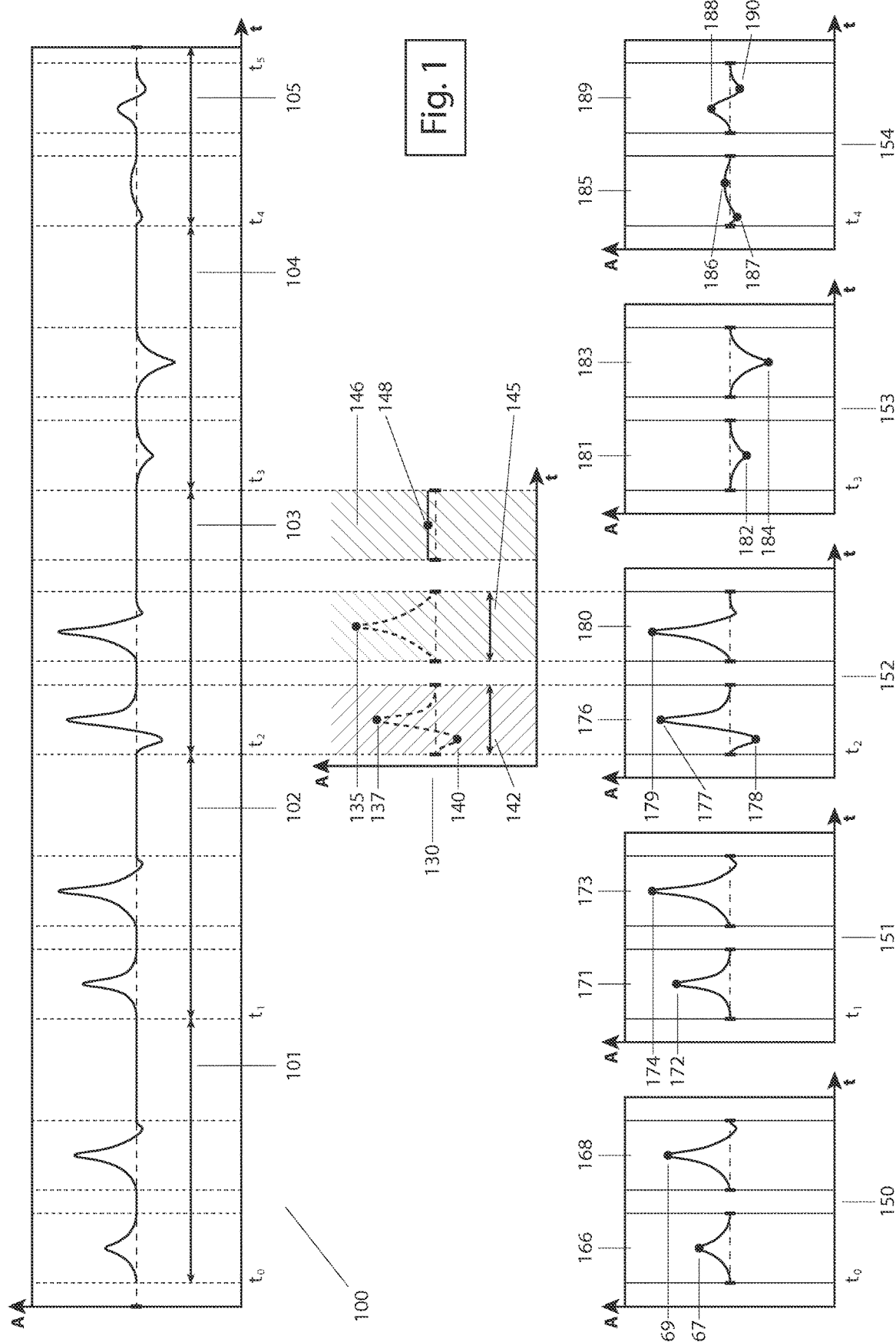
FIG. 1: Methods of extracting relevant features from patient data in real-time according to the present invention.

FIG. 1 illustrates a method for the extraction of relevant features from patient data in real-time according to the present invention. In one embodiment of the present invention, the graph 100 illustrates a sequence of 5 periods ($t_0$ through $t_4$) of a biological signal represented in the coordinate system Amplitude-Time (A-t). Such a signal can represent, for example, electrocardiogram (ECG), plethysmogram, pulse oximetry, blood pressure, etc. One of the characteristics of such signal is that it has a certain periodicity corresponding to the periodicity of body functions.

In one embodiment of the present invention, periodical signals are considered for feature extraction. In another embodiment of the present invention, signals are considered which are not periodical and happen at irregular time intervals. Traditionally, the variations in the amplitude of a signal are displayed on a time axis as illustrated by graph 100. For example, in Graph 100, a signal or waveform period 101 is illustrated starting at the moment $t_0$ and ending at moment $t_1$, followed by signal period 102 starting at $t_1$ and ending at $t_2$, period 103 starting at $t_2$ and ending at $t_3$, period 104 starting at $t_3$ and ending at $t_4$, and period 105 starting at $t_4$ and ending at $t_5$. One of the benefits of such a display (100) is that it allows for trend analysis, i.e., the user can follow the history of amplitude changes. One disadvantage of such display on a time axis is that it requires a relatively large real estate to be used for the display, e.g., a large screen or long print-outs in order to display a large enough number of signal periods. The amount of signal data increases even more in the case of patient monitoring, when such signals must be monitored and potentially recorded over long periods of time, i.e., days and weeks.

By observing the sequence of waveforms in Graph 100, one can notice that each period can be analyzed and certain relevant features extracted for each such period. In one embodiment of the present invention, FIG. 1, 130 illustrates certain relevant features which can be extracted from the signal sequence in Graph 100. It should be obvious for somebody skilled in the art that the illustrations in FIG. 1, 130 are not limitations of the present inventions and that other relevant features can be extracted from the signal in both time and frequency domains based on the same principles and with the same goals as described by the present inventions. It should further be obvious for somebody skilled in the art that a signal period can be divided into any number of relevant segments as well as any number of signal periods can be grouped into one segment of interest.

FIG. 1, 130 illustrates several relevant features of the periodic biological signal from Graph 100: a) the segments of interest 142, 145, and 146; b) the amplitude of interests 135 in segment 145, i.e., the maximum value of the signal in segment 145; the amplitudes of interest 137 and 140 in segment 142, i.e., the maximum and respectively the minimum values of the signal in segment 142; the average value of the signal 148 in segment 146.

The amplitudes of interest 135, 137, and 140 and the average value of the signal 148 can be determined in a number of ways as illustrated in the present invention. It should be obvious to somebody skilled in the art that such ways are not limitations of the present invention and that other ways to determine the amplitude of interest can be easily determined. In one embodiment of the present invention, the amplitude 135 is determined as the largest amplitude within a signal period.

In another embodiment of the present invention, the amplitude 135 is determined as the largest amplitude within a certain period of time after a steep increase in the signal as determined by computing the signal's first derivative or slope. In one embodiment of the present invention, amplitude 137 is calculate as the largest amplitude of the signal segment 142 and amplitude 140 is calculated as the smallest amplitude of the signal segment 142.

In another embodiment of the present invention, an average value 148 of the segment 146 is calculated and subtracted from the signal values in segments 142 and 145. In such an embodiment, the amplitude 135 is calculated as the largest positive value of segment 145, the amplitude 137 is calculated as the largest positive amplitude of segment 142 and the amplitude 140 is calculated as the largest negative amplitude of segment 142.

In one embodiment of the present invention, the average value 148 of segment 146 is calculated using equation 540 in FIG. 5.

The segments of interest 142, 145, and 146 can be determined in a number of ways as illustrated in the present invention. It should be obvious to somebody skilled in the art that such ways are not limitations of the present invention and that other ways to determine the segments of interest can be easily described. In one embodiment of the present invention, segment 145 is determined as being of a certain time length around the maximum amplitude 135 determined as described above herein. In one embodiment of the present invention, the determination of the start, end, and duration of segment 145 is made based on known physiological behavior generating the patient data/signal. For example, in the case of the signal being an ECG signal and the maximum amplitude 135 being an R-peak, the typical start, end and duration of segment 145 are determined by the activity of the atrio-ventricular node and are documented in the literature.

In one embodiment of the present invention, segment 146 is identified as the period of time with no or little activity of the signal, i.e., the period of time in which the amplitude of the signal is constant or quasi-constant. In one embodiment of the present invention, equation 510 in FIG. 5 is used to compute the signal variance and to determine the presence or lack of activity if the variance goes above or stays below a certain threshold, respectively.

In another embodiment of the present invention, the lack of activity in segment 146 is determined if the differences between the largest and the smallest of the amplitudes of consecutive or quasi-consecutive samples remain below a certain threshold.

In one embodiment of the present invention, the determination of the start, end, and duration of segment 142 is determined from known physiological behavior generating the patient data/signal. For example, in the case of the signal being an ECG signal and the maximum amplitude 135 being an R-peak, the typical start, end and duration of segment 142 are determined by the activity of the sino-atrial node and are documented in the literature as the P-segment and the P-wave. In another embodiment of the present invention, segment 142 and 145 are adjacent. Segment 142 ends and segment 145 starts at or at a certain time interval before the signal reaches its minimum amplitude value between the moment when it reaches amplitude 137 and the moment when it reaches amplitude 135.

A signal period, e.g. periods 101 through 105 can be identified in number of ways as illustrated in the present invention. It should be obvious to somebody skilled in the art that such ways are not limitations of the present invention and that other ways to determine the signal period can be easily determined.

In one embodiment of the present invention, a signal period is considered to start when the slope of the signal curve calculated as the signal's first derivative surpasses a certain threshold. The signal period is considered to stop when the subsequent signal period starts. In another embodiment of the present invention, a signal period is considered to start when the amplitude 135 is detected and last until the next (subsequent) amplitude 135 is detected. The duration of the signal period is measured in seconds and is computed by dividing the number of signal samples of the signal period by the sampling rate.

The method of extraction of relevant features from patient data as illustrated herein is not a limitation of the present invention. It should be obvious to somebody skilled in the art that other methods for feature extraction can be applied with a twofold purpose: a) to minimize the amount of information needed to be presented to the user and b) to minimize and/or simplify the presentation of time-dependent data. Such feature extraction methods can be morphological, statistical, and computational and other artificial intelligence methods, including adaptive and auto-adaptive methods, obvious to somebody skilled in the art. They can be applied in the time domain, in the frequency domain (using the Fourier Transform), or in another domain obtained by data transformation, e.g. principal component analysis (using the Karhunen-Loeve Transform). The relevant feature extraction according to the present invention does act as a practical data compression and principal components analysis algorithm, i.e., instead of having to interpret the entire sequence of patient data, one can interpret only the relevant features extracted. Thus, the system display and the user/system interaction can be simplified as described herein.

In one embodiment of the present invention, morphological or descriptive methods are used for feature extraction including: maximum and minimum signal amplitudes, signal slopes, presence or lack of signal changes, sequence of certain signal elements like amplitudes, segments, and slopes, identification of signal segments based of specific segment characteristics. In another embodiment of the present invention, statistical features are extracted from the signal including statistical moments of first and second order, e.g., a) average signal values over a signal segment, over a signal period or over multiple signal segments and periods, e.g., computed according to FIG. 5, 540; b) signal variance over a signal period or over multiple signal segments and periods, e.g., computed according to FIG. 5, 510; c) signal correlation over a signal period or over multiple signal segments and periods, e.g., computed according to FIG. 5, 520.

In another embodiment of the present invention, new features are calculated based on extracted features from the data, as for example, illustrated in FIG. 5 by 530, whereby $A_M$ may correspond to amplitude 135, $P_{M+}$ may correspond to amplitude 137, $P_{M-}$ may correspond to amplitude 140, and $T_M$ may correspond to amplitude 148 or to another amplitude of interest of another segment of interest in the signal period. The changes in relevant features extracted from the signal from period to signal period and over longer periods of time can be displayed in a simplified manner according to the present invention as shown further herein.

Figure 8:
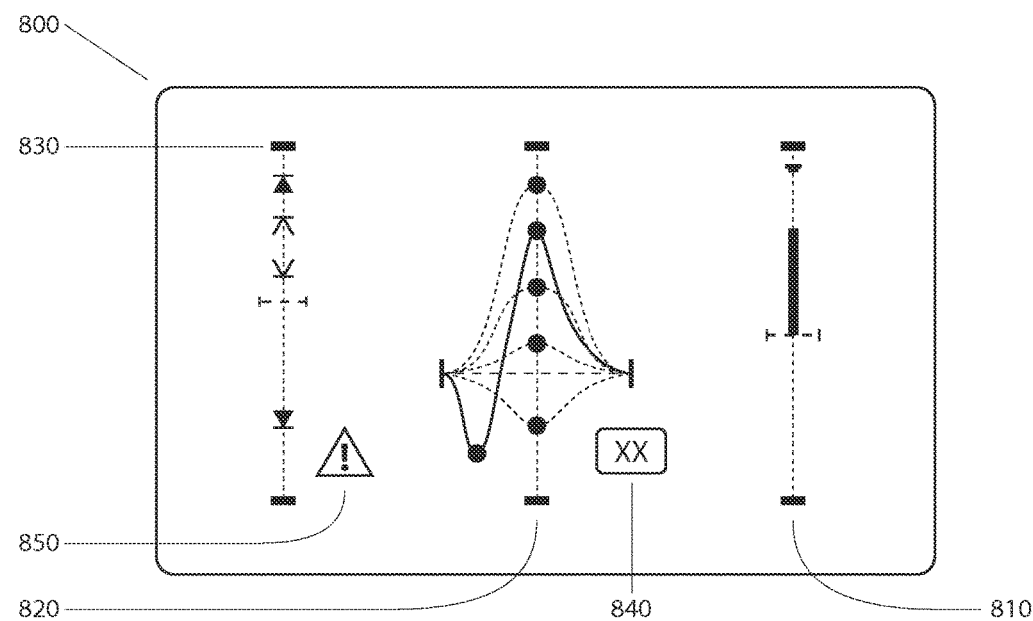
FIG. 8: Simplified user interface showing both time-dependent patient data and relevant features according to the present invention.

For example, in one embodiment of the present invention, the values of the signal variance in segment 142 can be displayed and certain changes in the signal variance can be interpreted to reflect medical conditions or specific data acquisition locations in the body. In another embodiment of the present invention, the computed feature according to 530 in FIG. 5 may be displayed in a simplified manner as illustrated in FIG. 8.

Correspondingly, Graph 100 can be redrawn as illustrated by Graphs 150 through 154, signal period by signal period by taking into account the relevant features illustrated by Graph 130. Graph 150 corresponds to the signal period starting at $t_0$ with its two relevant segments 166 and 168 and its relevant amplitude 167 for segment 166 and amplitude 169 for segment 168. Similarly, Graph 151 corresponds to the signal period starting at $t_1$ with its two relevant segments 171 and 173 and its relevant amplitude 172 for segment 171 and amplitude 174 for segment 173. Graph 152 corresponds to the signal period starting at $t_2$ with its two relevant segments 176 and 180 and its relevant amplitude 178 and 177 for segment 176 and amplitude 179 for segment 180. Graph 153 corresponds to the signal period starting at $t_3$ with its two relevant segments 181 and 183 and its relevant amplitude 182 for segment 181 and amplitude 184 for segment 183. And Graph 154, which corresponds to the signal period starting at $t_4$ with its two relevant segments 185 and 189 and its relevant amplitude 186 and 187 for segment 185 and amplitudes 188 and 190 for segment 189.

According to the present invention, graphs 150 through 154 do not need to be displayed at the same time on the same screen but can be displayed one after another on the screen. Tus, a smaller screen can be used to display the data from sequence of Graphs 150-154 instead of using Graph 100. Second, by extracting the relevant features from the patient data in Graph 100 as illustrated by Graph 130, according to the present invention, only the relevant segments and amplitudes need to be displayed and not all the patient data in Graph 100. Thus, according to the present invention, a smaller screen can be used to display the data by displaying only the relevant features instead of all the data. As a result, according to the present invention, a) the original sequence of patient data (signal) was compressed, i.e. reduced to a lesser number of relevant elements and b) the time-dependency of the patient data can be displayed in a simplified way in order to allow for the use of a smaller layout and screen real estate.

Figure 2:
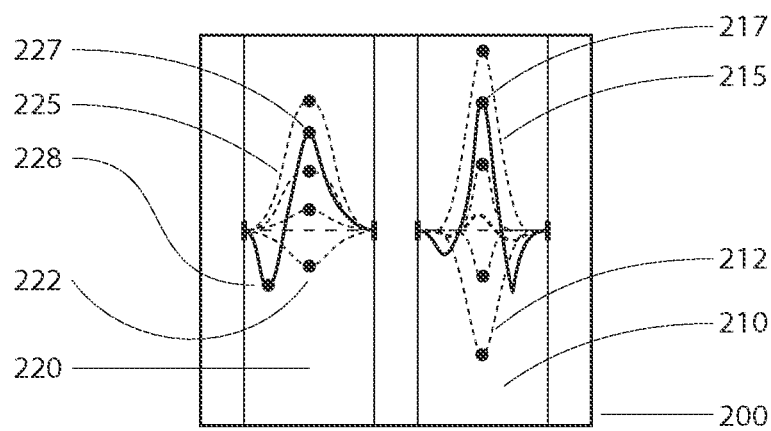
FIG. 2: Displaying time-dependent patient data using a simplified time coordinate according to the present invention.

FIG. 2 illustrates displaying time-dependent patient data using a simplified time coordinate according to the present invention. The Graphs 150 through 154 from FIG. 1 are superimposed on the same Graph 200. In one embodiment of the present invention, graphs 150 through 154 are aligned at a fix point on the display. In one embodiment of the invention, the maximum amplitude 135 in FIG. 1 is used to align these graphs by always displaying the time of the amplitude 135 at the same location (abscissa) on the screen.

In one embodiment of the present invention, superimposing graphs on the same screen as illustrated by FIG. 2 also corresponds to the history of the signal periods, i.e., the graphs corresponding to each signal period are superimposed one behind the other in the order of their temporal moments with the most recent signal period in front. Any number of signal periods from Graph 100 in FIG. 1 can be transformed into individual graphs as illustrated by Graphs 150 through 154 in FIG. 1 and then superimposed on the same graph as illustrated by Graph 200 in FIG. 2. The Graph 200 illustrates two relevant signal segments 220 and 210 as they have been identified in Graphs 150 (166 and 168) through 154 (185 and 189). The corresponding signals and relevant features illustrated in Graphs 150 through 154 from FIG. 1 are superimposed on Graph 200. The signal at time moments $t_0$ through $t_4$ are represented by 225 in segment 220 and by 215 in segment 210. The relevant amplitudes are represented by 227 and 228 in segment 220 and by 217 in segment 210.

In one embodiment of the present invention, the most recent signal corresponding to signal period at moment $t_4$ is represented by a full line while the waveforms corresponding to signal periods at prior moments $t_0$ through $t_3$ are represented by dotted lines (222 in segment 220 and 212 in segment 210). Any number of signal periods at any number of moments can be superimposed on the same Graph illustrated by 200.

In another embodiment of the present invention, the waveforms corresponding to different signal periods at different moments in time are represented by different colors. In another embodiment of the present invention, the waveforms at more recent moments are presented in brighter (higher intensity) colors while the waveforms at past moments are represented with fading colors such that the most recent waveform has the brightest color. In another embodiment of the present invention, the different waveforms at different moments are represented using different shades of gray. The purpose of this display layout is to emphasize the display on the same display area of the relevant features at the current moment in time, e.g., relevant amplitudes while showing at the same time some history of the waveforms at some previous moments in time.

In one embodiment of the present invention, the Graph displayed in FIG. 2 is updated with every new signal period showing the most recent and several past most recent relevant features and waveforms.

Figure 3:
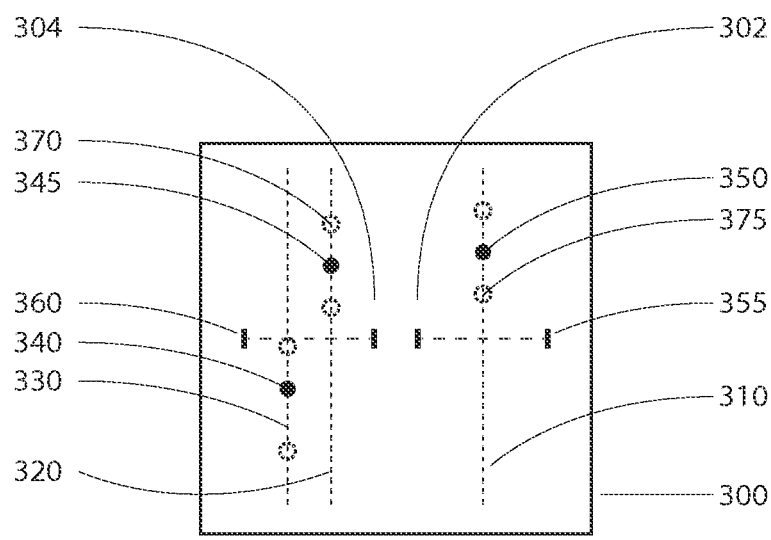
FIG. 3: One simplified display of relevant features of patient data according to the present invention.

FIG. 3 illustrates one simplified display of patient data according to the present invention. In display 300 only the relevant features extracted from patient data are displayed. In one embodiment of the present invention, relevant amplitudes are displayed for two segments of interest 302 and 304. In one embodiment of the present invention, the amplitudes at the current moment in time are displayed as full dots, 340 and 345 for segment 304 and 350 for segment 302 respectively. In one embodiment of the present invention, the amplitudes at two previous moments in time are displayed as dotted circles 370 for segment 304 and 375 for segment 302.

In one embodiment of the present invention, the dotted line 310 identifies the amplitude of interest 217 from FIG. 2 or amplitude 135 from FIG. 1. In one embodiment of the present invention, the dotted line 320 identifies the amplitude of interest 227 in FIG. 2 or 137 in FIG. 1 and the dotted line 330 identifies the amplitude of interest 228 in FIG. 2 or 140 in FIG. 1. In one embodiment of the present invention, the graph displayed in FIG. 3 is updated with every new signal period and shows the most recent and several past most recent relevant features.

In one embodiment of the present invention, the levels 355 and 360 represent the average value 148 from FIG. 1. In another embodiment of the present invention, the levels 355 and 360 represent another reference value, e.g., the value zero.

Figure 4:
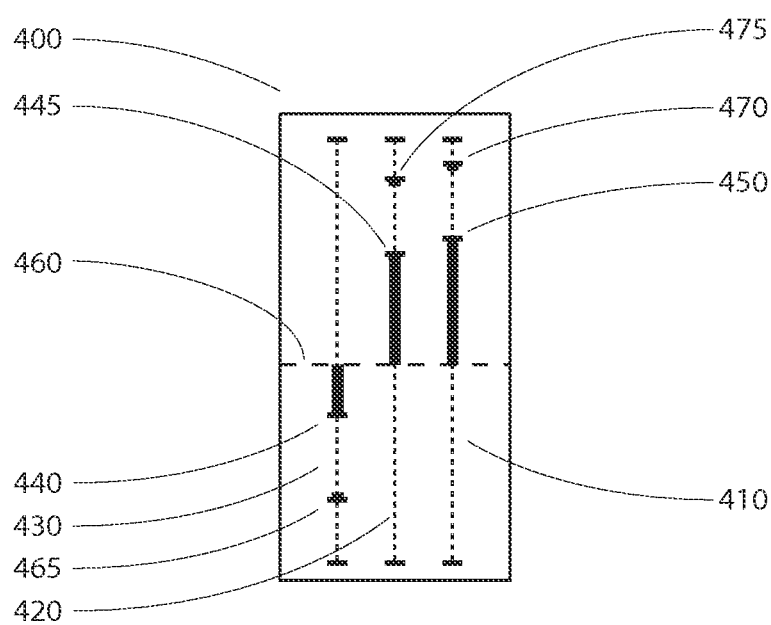
FIG. 4: Another simplified display of relevant features of patient data according to the present invention.

FIG. 4 illustrates another simplified display of relevant features of patient data according to the present invention. The Graph 400 in FIG. 4 does not show any more the relevant data segments identified by 130 in FIG. 1.

In one embodiment of the present invention, Graph 400 displays only the relevant features as intensity bars. In one embodiment of the present invention, intensity bar 410 represents the amplitude of interest 217 from FIG. 2, intensity bar 420 represents the amplitude of interest 227 from FIG. 2 and intensity bar 430 represents the amplitude of interest 228 from FIG. 2.

In another embodiment of the present invention, an intensity bar represents the value computed according to equation 530 in FIG. 5.

In another embodiment of the present invention, intensity bars represent the value computed according to equations 510 and or 520 in FIG. 5. In one embodiment of the present invention, the level of the intensity bar corresponds to the most current value of the relevant feature, value 450 for feature represented by the bar 410, value 445 for the feature represented by the bar 420 and value 440 for the feature represented by the bar 430.

In one embodiment of the present invention, the level 460 represents the average value 148 from FIG. 1. In another embodiment of the present invention, the level 460 represents another reference value, e.g., the value zero. In one embodiment of the present invention, markers are used to indicate the maximum maximorum value attained by relevant features in time, e.g., marker 470 for feature 410, marker 475 for feature 420. In one embodiment of the present invention, marker 465 indicates the minimum minimorum value attained by feature 430.

In one embodiment of the present invention, the intensity bars and the maximum maximorum and minimum minimorum values displayed in FIG. 4 are updated with every new signal period.

FIG. 5 illustrates algorithms used to support relevant feature extraction from patient data according to the present invention. In one embodiment of the present Invention, the standard deviation of the signal Sxj is computed according to 510, whereby n represents the number n of data samples $x_i$ for the j-th signal period, i=1,n. The value $^-x$ represents the average value of the data samples over the j-th signal period 540. The standard deviation computed according to 510 is a measure of the variations of the signal values around its average value during a signal period.

In one embodiment of the present invention, the auto-correlation coefficient $Cx_{j,j-1}$ is computed according to 520 for the signal x at the j-th signal period and at the previous j-1 signal period, whereby n represents the number of data samples $x_i$ for the j-th signal period, i=1,n. The value $^{-x}_j$ represents the average value of the data samples over the j-th signal period computed according to 540. The value $-x_{j-1}$ represents the average value of the data samples computed according to 540 over the j-1-th signal period, i.e., of the one signal period before the j-th heart cycle. $Sx_j$ is the standard deviation of the signal computed according to 510 for the j-th signal period. $Sx_{j-1}$ is the standard deviation of the signal computed according to 510 for the j-1-th signal period. In general, the number of samples n for the j-th signal period is different than the number of samples for the j-1-th signal period.

According to the present invention, n samples are considered for the calculation of both $Sx_j$ and $Sx_{j-1}$, whereby n is the number of samples of the j-th signal period. In another embodiment of the invention, the auto-correlation coefficient can be calculated using 520 as $Cx_{j,k}$, whereby j and k are any two signal periods. This includes the situation in which j=k and the coefficient is calculated for the same signal period.

In one embodiment of the present invention, the auto-correlation coefficient 520 is used to filter out signal periods very different from one another. It is assumed that, under normal conditions, the signal periods have a certain degree of similarity to each other. In the presence of noise or other artifacts or in case of malfunctions, the signal periods may be very different from one another. The auto-correlation coefficient 520 is used to estimate the degree of similarity between signal periods. A higher auto-correlation coefficient indicates a higher degree of similarity between two signal periods than a lower auto-correlation coefficient. Thus, if the auto-correlation coefficient of two signal periods is below a certain threshold, it can be considered that the two signal periods are weakly correlated or uncorrelated. In such a case, which may occur, for example, due to electromagnetic interference, the two signal periods are excluded from the computation of relevant features. With other words, according to the present invention, only signal periods which have a reasonable degree of similarity are considered for the extraction of relevant features.

In one embodiment of the present invention, one relevant feature computed from the signal is the sum $\Sigma_M$ of maximum relevant amplitudes of the signal for each signal period. In one embodiment of the present invention, the sum $\Sigma_M$ is calculated according to equation 530 in FIG. 5, whereby $A_M$ is the maximum amplitude of the signal in the segment of interest 145 in FIG. 1, $P_{M+}$ is the maximum positive amplitude of the signal aligned with the segment of interest 142 in FIG. 1, $P_{M-}$ is the maximum negative amplitude of the signal aligned with the segment of interest 142 in FIG. 1, and $T_M$ is the maximum amplitude of the signal aligned to another segment of interest of the signal period, for example with the segment 146 in FIG. 1.

In another embodiment of the present Invention, the sum $\Sigma_M$ is calculated as: $\Sigma_M = A_M + P_{M+} + P_{M-}$.

In another embodiment of the present invention, $T_M$ is the average value of the signal in segment 146 in FIG. 1 and the value $\Sigma_M$ is calculated as: $\Sigma_M = A_M + P_{M+} + P_{M-} - T_M$.

In one embodiment of the present invention, the parameters in FIG. 5, i.e., the standard deviation 510, the auto-correlation 520, the sum of relevant amplitudes 530, and the average value 540 are computed for a signal period. In another embodiment of the present invention, the parameters in FIG. 5 are computed for several consecutive signal periods. In another embodiment of the present invention, the parameters in FIG. 5 are computed for a fraction of a signal period, e.g., only for an interval/segment of interest within a signal period.

Figure 6:
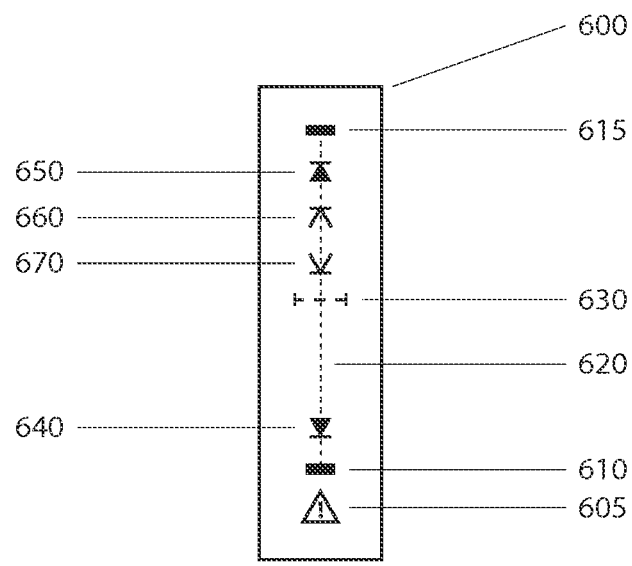
FIG. 6: Simplified user interface showing changes in relevant patient data features and tracking history of such changes according to the present invention.

FIG. 6 illustrates a simplified user interface showing changes in relevant features and tracking history of such changes according to the present invention. Values of a relevant feature are represented on the axis 620. Such a relevant feature can be any of the relevant features extracted from the patient data as described herein.

In one embodiment of the present invention, a relevant feature may be an amplitude of interest.

In another embodiment, a relevant feature may be the sum computed according to 530 in FIG. 5.

In one embodiment of the present invention only one relevant feature is displayed as illustrated by display 600.

In another embodiment of the present invention, several relevant features are displayed at the same time on a same screen using one display 600 for each of the relevant features. The level 630 illustrates the reference level of the values of the relevant feature. The icon 605 representing a warning sign is displayed whenever an issue is detected regarding the computation of the value of the relevant feature. In one embodiment of the present invention, a warning sign may be displayed if the auto-correlation coefficient calculated according to 520 in FIG. 5 decreases below a certain threshold. The warning sign can be displayed in different ways in different embodiments of the present invention.

In one embodiment of the present invention, an audible warning signal is also generated when a warning signal is displayed. The marker 610 represents the lower acceptable limit of the value range for the values of the relevant feature and the marker 615 represents the upper acceptable limit of the value range. In one embodiment of the present invention, the corresponding marker changes appearance whenever the value of the relevant feature is less than the lower limit or larger than the upper limit, in order to indicate that the value of the relevant feature is outside the acceptable range.

In one embodiment of the present invention markers 610 and 615 turn yellow whenever the value of the relevant feature is less than the lower limit 610 or larger than the upper limit 615. A graphical warning signal may be displayed and/or an audible warning signal may be generated according to the present invention whenever the value of the relevant feature is outside the acceptable range. The markers 640 and 650 are history markers. Marker 640 represents the minimum value within the acceptable range, i.e., within the limits 610 to 615, which the relevant feature has attained during a certain period of time, i.e., the minimum minimorum value. Correspondingly, marker 650 represents the maximum value within the acceptable range, i.e., within the limits 610 to 615, which the relevant feature has attained during a certain period of time, i.e., the maximum maximorum value.

In one embodiment of the present invention, the purpose of the markers 660 and 670 is twofold. On one hand, a marker 660 or 670 shows the current value of the relevant feature on the axis 620. On the other hand, a marker 660 or 670 shows the direction/trend of the change of the value since the last display.

In one embodiment of the present invention, if the current value of the relevant feature is larger than the previous value, then the marker 660 pointing upwards is displayed at the level of the current value on axis 620. If the current value of the relevant feature is smaller than the previous value then the marker 670 pointing downwards is displayed at the level of the current value on axis 620. In another embodiment of the present invention, only the current value of the relevant feature is displayed on the axis 620 without the display of the change/trend.

In another embodiment of the present invention, the trend analysis of the values of the relevant features takes into account filtering and averaging to allow for a more accurate determination of the trend than by only considering the difference between the current and the previous values of the relevant feature.

Figure 7:
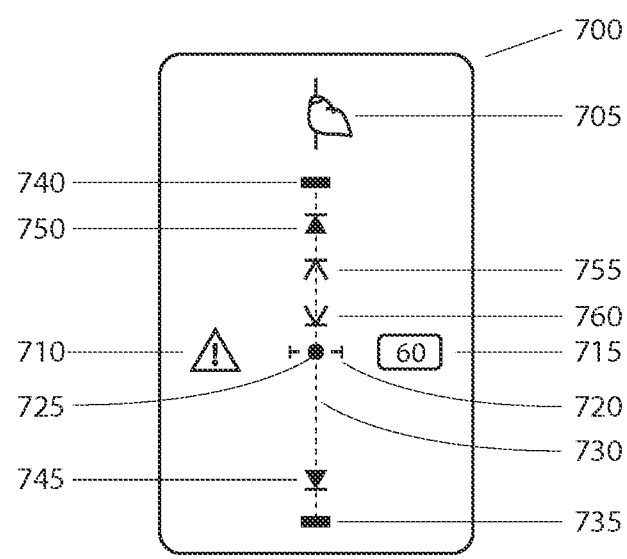
FIG. 7: Using the user interface according to the present invention for catheter guidance.

FIG. 7 illustrates one embodiment of the present invention applied to catheter guidance using the electrical conduction system of the heart and one control electrode placed over the manubrium of the sternum.

In the embodiment of the present invention illustrated in FIG. 7, the signal illustrated in FIG. 1 is a navigation signal computed from the intravascular ECG signal at the tip of the catheter and the skin ECG signal at the control electrode.

In this embodiment, the segment of interest 142 identified in FIG. 1 is aligned with the P-segment of the patient's ECG waveform, the segment 145 identified in FIG. 1 is aligned with the QRS complex of the patient's ECG waveform, and the segment 146 identified in FIG. 1 is aligned with the baseline segment of the patient's ECG waveform between the T and P segments. The relevant feature displayed on axis 730 of display 700 is the sum $\Sigma_M$ calculated as $\Sigma_M = A_M +$ $P_{M+}+P_{M-}$, whereby $A_M$ is the maximum amplitude of the navigation signal in the segment of interest aligned with the QRS complex of the ECG waveform, $P_{M+}$ is the maximum positive amplitude of the navigation signal aligned with the P-segment of the ECG waveform, and $P_{M-}$ is the maximum negative amplitude of the navigation signal aligned with the P-segment of the ECG waveform.

In one embodiment of the present invention, the reference level 720 represents the value of $\Sigma_M$ when the tip of the catheter is closest to the control electrode.

In another embodiment of the present invention, the reference level 720 represents the average value 148 of segment 146 in FIG. 1, i.e., the average value of the ECG baseline.

In yet another embodiment of the present invention, the reference level 720 has the value zero, which means that values below the reference level 720 are negative and values above the reference level 720 are positive. The display 715 displays the heart rate in beats per minute computed from the ECG signal period determined from the ECG signal at the control electrode with one of the methods described in FIG. 1. The signal period is measured in seconds and the heart rate in beats per minute is computed as one over the signal period and divided by 60.

In one embodiment of the present invention, the heart rate is calculated for each new signal period.

In another embodiment of the present invention, the heart rate is calculated as an average value over several signal periods and after exclusion of the uncorrelated signal periods based on the auto-correlation criterion described in FIG. 5.

In one embodiment of the present invention, the icon 710 represents a warning sign displayed whenever an issue is detected regarding the computation of $\Sigma_M$.

In one embodiment of the present invention, the warning sign is displayed if the auto-correlation coefficient calculated according to 520 in FIG. 5 decreases below a certain threshold. The warning sign can be displayed in different ways in different embodiments of the present invention. In one embodiment of the present invention, an audible warning signal is also generated when a warning signal 710 is displayed.

In one embodiment of the present invention, the icon 705 illustrates a heart on which the cavo-atrial junction is visibly marked. The location of icon 705 on the display 700 at the top of the axis 730 signifies the fact that, the closer the value displayed on the axis is to the icon, the closer the catheter tip is to the cavo-atrial junction.

In one embodiment of the present invention, icon 725 illustrates the relative location on the axis 730 of values of the navigation signal corresponding to the tip of the catheter in the proximity of the control electrode. With other words, whenever the value $\Sigma_M$ shown on axis 730 is close to icon 725, then the tip of the catheter is close to the control electrode.

In one embodiment of the present invention, the marker 725 turns blue whenever the value $\Sigma_M$ shown on axis 730 is close to the reference level 720. In one embodiment of the present invention, a symbol is represented in the color blue indicating the reference level 720. The marker 735 indicates the lowest acceptable value $\Sigma_M$ which can be displayed without distortions and the marker 740 indicates the highest acceptable value $\Sigma_M$ which can be displayed without distortions. All values of $\Sigma_M$ higher than the marker 740 are represented at the level of marker 740 and all values of $\Sigma_M$ lower than the marker 735 are represented at the level of marker 735 on the axis 730. Such situations can happen, for example in the case of inappropriate selection of signal scale and in case of electromagnetic interferences. In such situations, a warning signal 710 is displayed and the user can correct the situation by selecting an appropriate signal scale or eliminating the cause of electromagnetic interference.

In one embodiment of the present invention, a warning signal 710 is also displayed if the auto-correlation coefficient 520 in FIG. 5 is below a certain threshold. The marker 745 represents the minimum minimorum value of $\Sigma_M$ recorded during the course of a catheter placement procedure and the marker 750 represents the maximum maximorum value of $\Sigma_M$ recorded during the course of a catheter placement procedure.

In one embodiment of the present invention, initially, i.e., in the beginning of the catheter placement procedure, the values represented by 745 and 750 are zero. For each signal period, a current positive value of $\Sigma_M$ is compared with the value represented by 750. If the current value of $\Sigma_M$ is larger than the value represented by 750 then the value represented by 750 is updated with the current value of $\Sigma_M$. Thus the value 750 always represents the largest attained value of $\Sigma_M$. Similarly, for each signal period, a current negative value of $\Sigma_M$ is compared with the value represented by 745. If the current value of $\Sigma_M$ is smaller than the value represented by 745 then the value represented by 745 is updated with the current value of $\Sigma_M$. Thus, 745 always represents the smallest (or the largest negative) attained value of $\Sigma_M$.

In one embodiment of the present invention, the value of $\Sigma_M$ is represented on the axis 730 as either an upwards pointing arrow as illustrated by 755 or a downwards pointing arrow as illustrated by 760. The horizontal line of the icons 755 and 760 represent the current value of $\Sigma_M$ on the axis 730. The arrow of icons 755 and 760 represent the trend in the change of the value, either from the last update or during a certain period of time. If the arrow points upwards as illustrated by icon 755, then the current value of $\Sigma_M$ represents an increase in value compared to a previous value or average value or trend of value change. If the arrow points downwards as illustrated by icon 760, then the current value $\Sigma_M$ represents a decrease in value compared to a previous value or average value or trend of value change.

In one embodiment of the present invention, the markers 755 and 750 are displayed in green in order to indicate a desired trend in the values displayed on axis 730. In one embodiment of the present invention, the markers 760 and 745 are displayed in red in order to indicate an undesired trend in the values displayed on axis 730.

In one embodiment of the present invention markers 740 and 735 turn to yellow whenever the value of the relevant feature is less than the lower limit 735 or larger than the upper limit 740 in order to indicate a warning condition.

In one embodiment of the present invention, audible signals or sequences of audible signals of different frequencies and intensities are generated when any of the markers 725, 735, 740, 745, 750, 755 or 760 changes colors.

FIG. 8 illustrates a simplified user interface showing both time-dependent patient data and the display of relevant features according to the present invention.

In one embodiment of the present invention, the display 800 contains the following elements: a) a display 810 of a relevant feature using intensity bars as illustrated in FIG. 4; b) a display 820 of patient signals in the simplified format illustrated in FIG. 2; c) a display 830 of a relevant feature showing value tracking and display history as illustrated in FIG. 6; d) a numerical display of patient information 840 as illustrated in FIG. 7; and a warning signal 850 as illustrated in FIGS. 6 and 7.

In one embodiment of the present invention, the elements 810, 820, and 830 of the display 800 represent the same relevant feature.

In another embodiment of the present invention, the elements 810, 820, and 830 of the display 800 represent different relevant features, e.g., the display 820 represents the patient's ECG waveforms and their relevant amplitudes, display 830 represents the relevant feature $\Sigma_M$ as described in FIG. 7, the intensity bar 810 displays the patient's oxygen saturation, the field 840 displays the heart rate and the warning signal 850 relates to thresholds of the patient's blood pressure. The display 800 is not a limitation of the present invention and it should be obvious to somebody skilled in the art that other display configurations are possible showing one or several or additional display elements as illustrated in FIG. 8. It should be further obvious to somebody skilled in the art that the display elements of the display 800 can refer to different types of patient information than those described herein.

Figure 9:
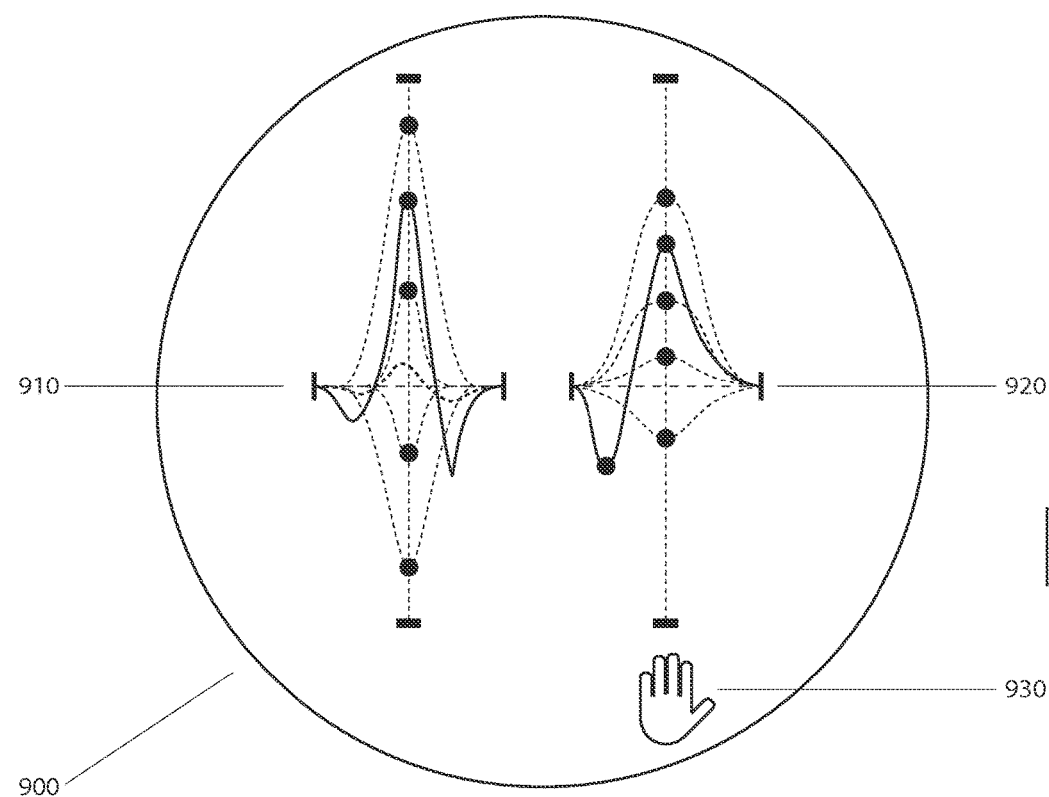
FIG. 9: Simplified user interface showing time-dependent patient data in real time and frozen as reference according to the present invention.

FIG. 9 illustrates a simplified user interface showing time-dependent patient data in real time and frozen patient data for reference according to the present invention. In certain clinical situations it is needed that the user can compare the currently displayed patient data with patient data displayed at a previous moment in time.

In one embodiment of the present invention, on display 900 in FIG. 9, real time data 910 is displayed in a similar manner as in FIG. 2. Frozen data at a previous moment in time is displayed by 920.

In one embodiment of the present invention, only the most recent signal period represented by a full line in display 910 is frozen for display by the display 920. In one embodiment of the present invention, the icon 930 has a twofold purpose. On a touch screen, the icon 930 serves as a Freeze button. Whenever the user taps on the icon 930, the current data displayed by 910 is copied to the display 920. The display 920 remains unchanged until the next time the user touches the icon 930 and new data is copied from display 910 to display 920. Icon 930 serves also to indicate to the user that the data in display 920 is frozen, i.e., it has been acquired at a previous moment in time.

In one embodiment of the present invention, double tapping on the icon 930 clears the display 920. In one embodiment of the present invention, the Freeze function illustrated in FIG. 9 can be achieved by voice control. By pronouncing the word "Freeze", the user performs the same action as tapping on icon 930. By pronouncing the word 'Clear", the user clears the display 920. In another embodiment of the present invention, the Freeze function illustrated in FIG. 9 can be implemented with any display or combination of displays and data as, for example, those illustrated in FIG. 8. The illustrations in FIG. 9 are not limitations of the current invention. It should be obvious to somebody skilled in the art that other types of data and patient information can be presented as a duality of real-time and frozen displays, whereas other icons and voice commands can be used to freeze data and clear the display.

Figure 10:
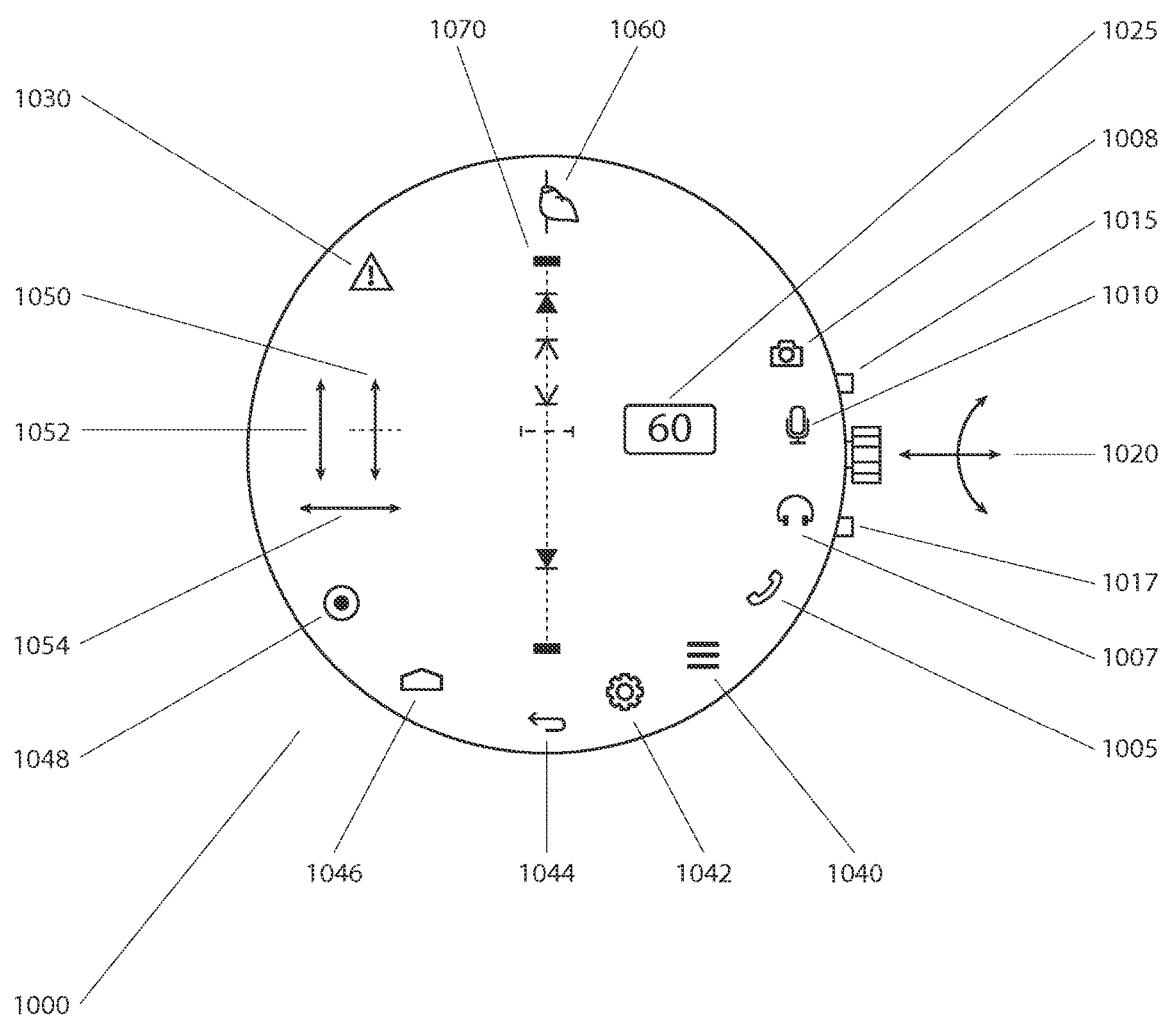
FIG. 10: Elements of a user interface and methods for user interaction according to the present invention.

FIG. 10 illustrates elements of a user interface and methods for user interaction according to the present invention.

In one embodiment of the present invention, the display 1000 illustrates several display and control elements.

In one embodiment of the present invention the display 1000 is also a touch screen. In one embodiment of the present invention, relevant features of patient data 1070 are displayed as illustrated in FIG. 7.

In another embodiment of the present invention, relevant features of patient data are displayed as illustrated in FIG. 8.

Relevant patient information may also be displayed as an alphanumeric field 1025. Icons, illustrated by 1060, may be displayed indicating the significance of the relevant features of interest displayed by 1070. A warning signal 1030 may be displayed as illustrated in FIGS. 6 and 7.

By using the touchscreen function of the display 1000, in one embodiment of the present invention, a method to scroll the reference level of 1070 up and down on the screen, for example swiping using one finger, is illustrated by 1050.

By using the touchscreen function of the display 1000, in one embodiment of the present invention, a method to increase and decrease the scale for the display 1070, for example using two fingers, is illustrated by 1052.

By using the touchscreen function of the display 1000, in one embodiment of the present invention, a method to increase and decrease the display update speed (or scroll speed) of display 1070, for example using two fingers, is illustrated by 1054.

In one embodiment of the present invention, by using the reset touchscreen button 1048, the user can reset to zero the values of the minimum minimorum and maximum maximorum markers of the display 1070.

In one embodiment of the present invention, several touchscreen icons are used to navigate different menus and screens of the user interface. Touching or tapping on icon 1046 navigates to the home screen, which in one embodiment of the invention is the display 1000. Touching or tapping on icon 1044 goes back one step in the navigation path. Touching or tapping on icon 1042 leads to a menu for settings. Touching or tapping on icon 1040 leads to a list of available menus, including a patient information menu.

In one embodiment of the present invention, touch icon 1005 allows the user to make a phone call while looking at the display 1000. In one embodiment of the present invention, when the user makes a phone call while displaying display 1000, the entire display or only the relevant feature display 1070 are duplicated on the screen of the receiving phone.

In one embodiment of the present invention, the user can receive and pick up a phone call while displaying display 1000 and the entire display or only the relevant feature 1070 are duplicated on the screen of the calling phone.

In one embodiment of the present invention, button 1020 provides additional methods for the interaction of the user with the device.

In one embodiment of the present invention, by rotating the button 1020 clockwise or counterclockwise, the user can increase or respectively decrease the scale of the display 1070. By pulling the button 1020 and then rotating it, the user can scroll up and down the reference level of display 1070. By pressing the button 1020, the user can reset to zero the minimum minimorum and the maximum maximorum values of display 1070. It should be obvious to somebody skilled in the art that other methods and relevant functionality can be implemented using one or several buttons like 1020.

In one embodiment of the present invention, icon 1007 illustrates a headphone and is displayed on display 1000 when a headphone is available for user interaction, for example by connecting an external headphone to the jack 1017.

In one embodiment of the present invention, the icon 1010 illustrates a microphone and is displayed on display 1000 when a microphone is available for user interaction, for example by connecting an external microphone to jack 1015.

In one embodiment of the present invention, if a microphone is available for interaction, a method for the user to interact with the display 1000 is by voice control. In one embodiment of the present invention, the word "Up" increases the scale of display 1070, the word "Down" decreases the scale of the display 1070, and the word "Reset" resets to zero the minimum minimorum and maximum maximorum values of display 1070.

In one embodiment of the present invention, touch icon 1008 allows the user to take a picture and or make a short movie while displaying display 1000.

In one embodiment of the present invention, such a picture or movie are transmitted to a receiving or calling phone if a phone call initiated using icon 1005 is in progress.

In one embodiment of the present invention, icon 1008 indicates when a camera is available for use with the display 1000. In the situation in which a camera is available for use, the user can use gestures as a method to interact with the display 1000.

In one embodiment of the present invention, waving the hand in front of the camera resets to zero the minimum minimorum and maximum maximorum values of display 1070. In one embodiment of the present invention, holding two fingers in front of the camera increases the scale of display 1070 while holding one finger in front of the camera decreases the scale of display 1070. In one embodiment of the present invention, holding the hand in front of the camera sends the relevant display data to a printer, if a printer is connected, for example by Bluetooth.

In one embodiment of the present invention the display, the interaction elements, and the interaction methods illustrated in FIG. 10 can be implemented using a cellphone.

In another embodiment of the present invention the display, the interaction elements, and the interaction methods illustrated in FIG. 10 can be implemented using a smart watch. In another embodiment of the present invention the display, the interaction elements, and the interaction methods illustrated in FIG. 10 can be implemented using a head-mounted display.

In another embodiment of the present invention the display, the interaction elements, and the interaction methods illustrated in FIG. 10 can be implemented using a Google glass.

In another embodiment of the present invention the display, the interaction elements, and the interaction methods illustrated in FIG. 10 can be implemented using other types of mobile and/or wearable devices.

The illustrations in FIG. 10 are not a limitation of the present invention. It should be obvious for somebody skilled in the art that other interaction elements, other functions, and other interaction methods can be implemented using the elements illustrated in FIG. 10.

Figure 11:
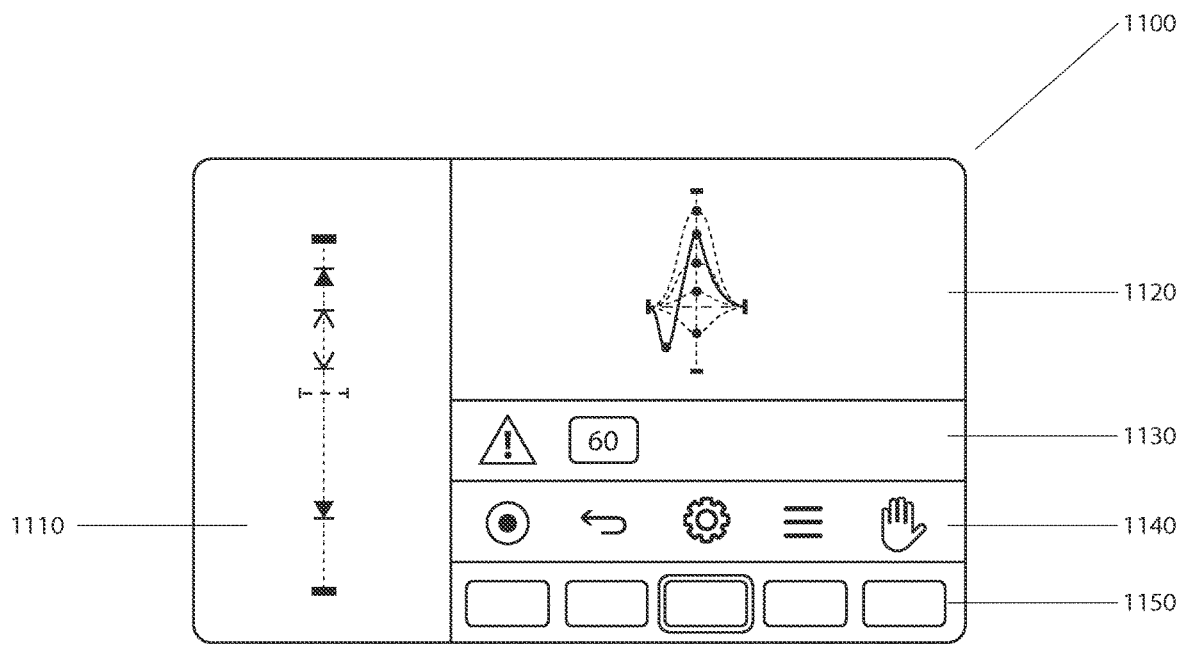
FIG. 11: Simplified user interface for a head-mounted device according to the present invention.

FIG. 11 illustrates a simplified user interface for a head-mounted device according to the present invention.

In one embodiment of the present invention, the display 1100 is a color 640×360 pixel display. In one embodiment of the present invention, the main display layout 1100 is divided into a left image or column for live information 1110, a field 1120 for static information, e.g., for frozen data or images, footer for supplementary information 1130, a menu bar 1140, and a status bar 1150.

In one embodiment of the present invention, the live information field 1110 displays relevant features of patient data as illustrated in FIG. 10, 1070.

In another embodiment of the present invention, the live information field 1110 displays relevant features of patient data are displayed as illustrated in FIG. 8.

In one embodiment of the present invention, the static field 1120 displays frozen images and patient data as illustrated in FIG. 9, 920.

In one embodiment of the present invention, the footer 1130 for additional information displays warning signs, time stamps, and other relevant information, e.g., the patient's heart rate as described in FIGS. 6 and 7.

In one embodiment of the present invention, the menu bar 1140 displays items as those described in FIG. 10, e.g., 1040, 1042, 1044 and 1048 and in FIG. 9, 930.

In one embodiment of the present invention, the status bar 1150 shows the current set of data being displayed, progress information for different user interactions, or other information related to system status, e.g., Bluetooth communication. The illustrations in FIG. 11 are not a limitation of the present invention. It should be obvious for somebody skilled in the art that other screen layouts and the display of other information and control elements are possible.

Figure 12:
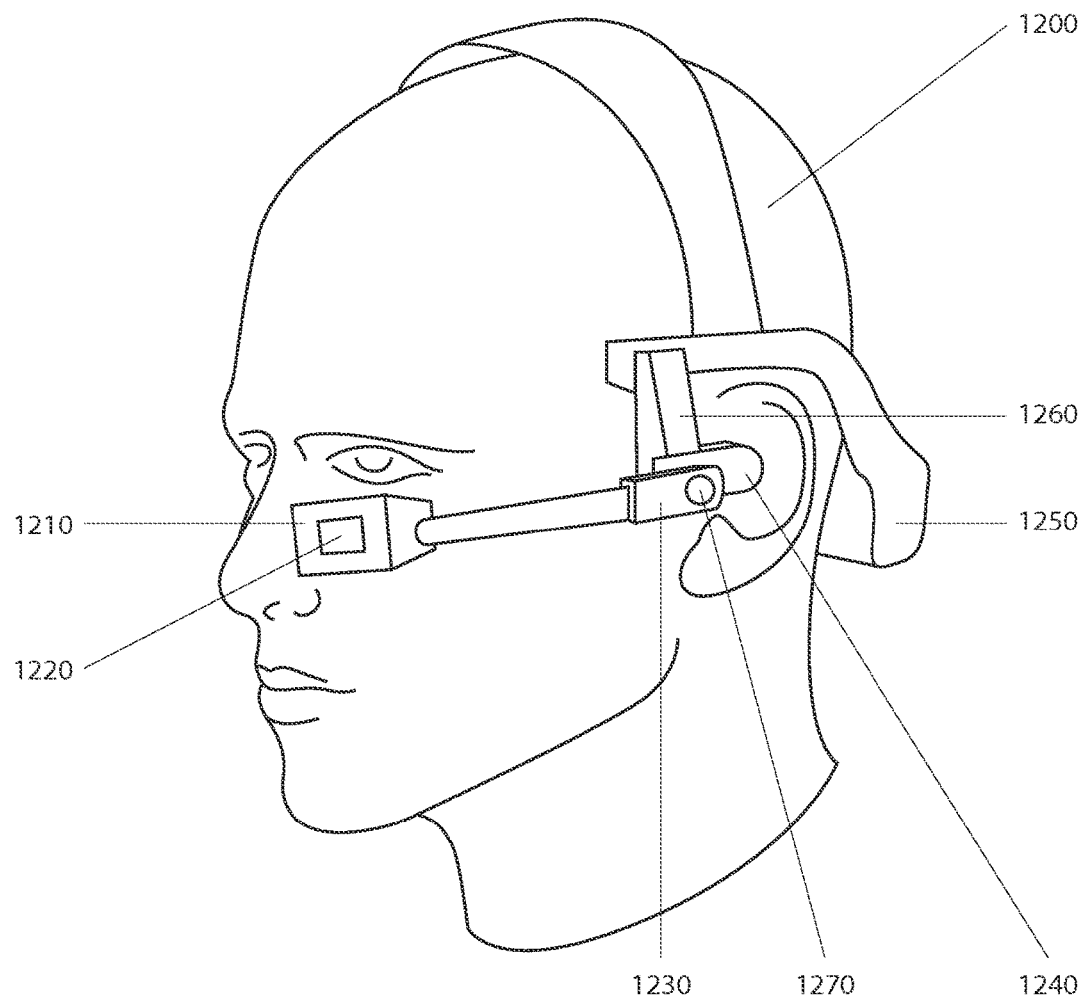
FIG. 12: Head-mounted device and methods for user interaction according to the present invention.

FIG. 12 illustrates a head-mounted device and methods for user interaction according to the present invention. In one embodiment of the present invention, a head-mounted device 1200 contains a display or screen 1210, a front video camera 1220, a microphone 1230, a headphone 1240, a lateral video camera 1270, battery, processing unit, and other sensors 1250, and a touchpad 1260.

In one embodiment of the present invention the unit 1250 includes a 3 axis gyroscope, a 3 axis accelerometer, an ambient light sensor, and a proximity sensor. In one embodiment of the present invention, the head-mounted device in FIG. 12 is a Google glass.

In one embodiment of the present invention, other wireless devices are connected to the head-mounted device, e.g., a Bluetooth printer, a smartphone, or a tablet.

In one embodiment of the present invention, the method of interaction between an operator and the head-mounted device is optimized for the use by a sterile operator, i.e., for an operator with sterile gloves operating in a sterile filed who cannot touch the head-mounted device.

In such an embodiment all interaction between the operator and the head-mounted device is based on voice, hand gestures, and head movements.

In one embodiment of the present invention, the touchpad 1260 allows the user to tap, to slide forward, backward, up, and down, and to swipe up and down. The user can scroll through items displayed on the screen by sliding one finger over the touchpad and select one item and by tapping on the desired item. If the user selects an item like the reference level of the display 1110, sliding up and down on the touchpad will move the reference level up and down on the display. Swiping down on the touchpad will go back to a previous screen. This action is similar to a back button as illustrated in FIG. 10, 1044.

In one embodiment of the present invention, tilting the head down will exit the application. Shaking the head left and right will move through a list of options displayed on the screen, e.g., like the one illustrated in FIG. 11, 1140 and holding the hand in front of a camera will select an item from that list.

In one embodiment of the present invention, waving the hand in front of the front or lateral camera will freeze an image as in FIG. 9 or will reset markers as in FIG. 10 depending on the display mode. Holding two fingers in front of the camera will increase the scale of the signal displayed by 1110 in FIG. 11 and holding one finger in front of the camera will decrease the signal scale. If in data display mode, holding the hand in front of a camera will send the current data displayed on the display to a connected device, e.g., to a printer, to a smartphone or to a tablet.

In one embodiment of the present invention, the head-mounted device in FIG. 12 can be controlled by voice. The word "Up" increases the scale of display illustrated by 1110 in FIG. 11, the word "Down" decreases the scale of the display 10110, and the word "Reset" resets to zero the minimum minimorum and maximum maximorum values of display 1110. The word "Patient" changes the static display 1120 to a patient information display and the word "Data" changes it back to displaying relevant data. The word "Back" has similar effects like the back button 1044 in FIG. 10. In one embodiment of the present invention, the head-mounted device can be taught new voice commands by initiating actions and associating words to them.

In one embodiment of the present invention, the headphone 1240 is used for audible warning signals generated as described herein, for example in FIG. 10.

The illustrations in FIG. 12 are not a limitation of the present invention. It should be obvious for somebody skilled in the art that other methods of interaction can be implemented using voice control, hand gestures, head movements and tapping and swiping on the touchpad.

What is claimed is:

1. A method for simplifying a display of signals, the method comprising:
    obtaining an electrocardiogram (ECG) signal with an electrode located at a tip of a catheter inserted into a body of a patient;
    identifying an ECG waveform from the ECG signal;
    extracting a set of relevant features of the ECG signal from each segment of interest of a plurality of segments of interest of the ECG waveform at different time periods,
    wherein:
        each of the plurality of segments of interest corresponds to a different time period, wherein each segment of interest corresponds to a particular time period, wherein an amplitude axis is illustrated as a single vertical plane, and wherein a plurality of visual indicators are illustrated in the single vertical plane, and
        each relevant feature of the set of relevant features is displayed as a visual indicator on the amplitude axis and illustrates at least one of:
            (i) a maximum amplitude measured for each segment of interest,
            (ii) a minimum amplitude measured for each segment of interest, or
            (iii) an average value of the ECG waveform within each segment of interest; and
    generating a display screen that includes the set of relevant features of each of the plurality of segments of interest superimposed on the amplitude axis, wherein the display screen is configured to emphasize relevant features of a most recent segment of interest of the plurality of segments of interest.

2. The method as defined in claim 1, wherein the display screen is configured for display on a touchscreen, wherein touch, input via touchscreen, controls displaying the set of relevant features.

3. The method as defined in claim 1, wherein the set of relevant features on the display screen is auto-adaptive as a function of information content of the ECG signal.

4. The method as defined in claim 1, wherein extracting the set of relevant features includes morphological analysis of signal characteristics in time or frequency domains.

5. The method as defined in claim 1, wherein extracting the set of relevant features includes statistical analysis of signal characteristics in time or frequency domains.

6. The method as defined in claim 1, wherein extracting the set of relevant features includes a reduction or selection of a number of features characterizing the ECG signal via a selective data compression.

7. The method as defined in claim 1, wherein extracting the set of relevant features includes a definition and computation of the set of relevant features based on a relevance analysis.

8. The method as defined in claim 7, wherein the definition and computation of the set of relevant features includes a definition and computation of sum and differences of amplitudes of a plurality of ECG waveforms.

9. The method as defined in claim 7, wherein the computation of the set of relevant features includes a computation of a standard deviation and of a correlation coefficient.

10. A method for displaying a location of a tip of an intravascular catheter, the method comprising:
    obtaining an electrocardiogram (ECG) signal with an electrode located at the tip of the intravascular catheter inserted into a body of a patient;
    identifying an ECG waveform from the ECG signal;
    extracting signed values of peak values of a R-wave, a positive P-wave, and a negative P-wave of the ECG signal from each segment of interest of a plurality of segments of interest of the ECG waveform at different time periods;
    computing a set of relevant features of the ECG waveform as a sum of extracted peak values; and
    generating a display screen that includes the set of relevant features of each of the plurality of segments of interest superimposed on an amplitude axis, wherein each segment of interest corresponds to a particular time period, wherein the amplitude axis is illustrated as a single vertical plane, wherein a plurality of visual indicators are illustrated in the single vertical plane, wherein the display screen is configured to emphasize the relevant features of a most recent segment of interest of the plurality of segments of interest, wherein the display screen is updated in real time with additional segments of interest, and wherein each relevant feature of the set of relevant features of the ECG waveform is displayed as a visual indicator on the amplitude axis and illustrates at least one of:
        (i) a maximum amplitude measured for each segment of interest,
        (ii) a minimum amplitude measured for each segment of interest, or
        (iii) an average value of the ECG waveform within each segment of interest.

11. The method as defined in claim 10, further comprising:
    responsive to determining the location of the tip of the catheter is outside of a predefined location range within the body based on at least the set of relevant features, updating the display screen to include a warning icon.

12. The method as defined in claim 10, further comprising:
    determining a trend of changes in the relevant features of one or more of the most recent segment of interest or a previous segment of interest; and
    updating, in real-time, the display screen to include a graphical representation of the trend of changes in the relevant features of one or more of the most recent segment of interest or a previous segment of interest.

13. The method as defined in claim 1, wherein each visual indicator is one of a dot or a dash.

14. The method as defined in claim 1, wherein each visual indicator represents a singular point in time.

15. A method performed in connection with a mobile medical device, comprising:
   obtaining an electrocardiogram (ECG) signal with an electrode located at a tip of a catheter inserted into a body of a patient;
   identifying an ECG waveform from the ECG signal;
   extracting a set of relevant features of the ECG signal from each segment of interest of a plurality of segments of interest of the ECG waveform at different time periods,
   wherein:
      each of the plurality of segments of interest correspond to a different time period, wherein each segment of interest corresponds to a particular time period, wherein an amplitude axis is illustrated as a single vertical plane, and wherein a plurality of visual indicators are illustrated in the single vertical plane, and
      each relevant feature of the set of relevant features is displayed as a visual indicator on the amplitude axis and illustrates at least one of:
         (i) a maximum amplitude measured for each segment of interest,
         (ii) a minimum amplitude measured for each segment of interest, and
         (iii) an average value of the ECG waveform within each segment of interest; and
   displaying one or more graphical elements representing the set of relevant features of each of the plurality of segments of interest superimposed on the amplitude axis on a display screen of the mobile medical device, wherein the display screen is configured to emphasize relevant features of a most recent segment of interest of the plurality of segments of interest.

16. The method as defined in claim 15, wherein the relevant features of the most recent segment of interest are emphasized over the set of relevant features of a previous segment of interest and are displayed without a time coordinate.

17. The method as defined in claim 15, wherein a history of changes over time of the relevant features of the most recent segment of interest and relevant features of a previous segment of interest are displayed using the one or more graphical elements, the displaying step further comprising displaying:
   a line including one or more symbols that indicate significant locations on the line, and
   a first symbol of the one or more symbols representing a value of a first relevant feature of the most recent segment of interest at a first point in time, wherein the first symbol representing the relevant feature is displayed on the line in real time.

18. The method as defined in claim 17, wherein the first symbol represents a trend of changes in the relevant features of the most recent segment of interest.

19. The method as defined in claim 17, wherein the mobile medical device includes a user interface on a touchscreen, the mobile medical device being configured to receive: (i) touch input to control the display of the relevant features including display scale and display speed, and (ii) touch input to control display settings and functions.

20. The method as defined in claim 19, wherein the user interface further comprises one or more icons representing transmission and receipt of one or more ECG signals, the mobile medical device configured for the transmission and receipt of one or more ECG signals or of relevant features to and from a second network device.

21. The method as defined in claim 15, wherein the ECG waveform and the relevant features of the most recent segment of interest are displayed simultaneously on a second network device.

22. The method as defined in claim 15, wherein each visual indicator is one of a dot or a dash.

23. The method as defined in claim 15, wherein each visual indicator represents a singular point in time.

24. The method as defined in claim 10, wherein the display screen configured to emphasize the relevant features of the most recent segment of interest corresponds to displaying the relevant features of the most recent segment of interest using one or more solid lines and displaying the relevant features of a previous segment of interest using one or more dotted lines.

25. The method as defined in claim 10, wherein each visual indicator is one of a dot or a dash.

26. The method as defined in claim 10, wherein each visual indicator represents a singular point in time.

* * * * *